(12) United States Patent
Nabeshima et al.

(10) Patent No.: US 10,279,150 B2
(45) Date of Patent: May 7, 2019

(54) GUIDEWIRE

(71) Applicant: TERUMO KABUSHIKI KAISHA, Shibuya-ku, Tokyo (JP)

(72) Inventors: Yousuke Nabeshima, Fujinomiya (JP); Yuusuke Sekine, Chigasaki (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 42 days.

(21) Appl. No.: 15/261,089

(22) Filed: Sep. 9, 2016

(65) Prior Publication Data
US 2016/0375226 A1 Dec. 29, 2016

Related U.S. Application Data

(63) Continuation of application No. PCT/JP2015/052516, filed on Jan. 29, 2015.

(30) Foreign Application Priority Data

Mar. 19, 2014 (JP) ................ 2014-057288

(51) Int. Cl.
*A61B 6/00* (2006.01)
*A61B 6/12* (2006.01)
*A61M 25/09* (2006.01)

(52) U.S. Cl.
CPC ............ *A61M 25/09* (2013.01); *A61B 6/485* (2013.01); *A61B 6/12* (2013.01);
(Continued)

(58) Field of Classification Search
CPC ........ A61M 25/09; A61M 2025/09091; A61M 25/09025; A61M 2025/09083; A61M 2025/0915; A61B 6/12
See application file for complete search history.

(56) References Cited

U.S. PATENT DOCUMENTS 4,940,062 A * 7/1990 Hampton ........ A61M 25/09033
600/434
5,480,382 A * 1/1996 Hammerslag ..... A61M 25/0053
600/585
(Continued)

FOREIGN PATENT DOCUMENTS

JP  H09-510125 A  10/1997
JP  2006-149804 A  6/2006
(Continued)

OTHER PUBLICATIONS

International Search Report (PCT/ISA/210) dated Mar. 24, 2015, by the Japanese Patent Office as the International Searching Authority for International Application No. PCT/JP2015/052516.
(Continued)

*Primary Examiner* — Sean P Dougherty
(74) *Attorney, Agent, or Firm* — Buchanan Ingersoll & Rooney PC (57) ABSTRACT

The disclosed guidewire includes a wire main body possessing an elongated shape and a cylindrical body possessing a cylindrical shape. The distal portion of the wire main body is positioned in the cylindrical body. The guidewire has an inner coil disposed between the wire main body and the cylindrical body. The inner coil includes a wire rod wound in a spiral shape along the outer circumferential portion of the wire main body. There is an interval between the wire rods adjacent to each other in a longitudinal direction of the wire main body that is adjustable. The guidewire also has an operation member that changes the interval between the wire rods of the inner coil.

17 Claims, 3 Drawing Sheets

(52) U.S. Cl.
CPC ............. *A61M 25/09025* (2013.01); *A61M 2025/0915* (2013.01); *A61M 2025/09083* (2013.01); *A61M 2025/09091* (2013.01); *A61M 2025/09166* (2013.01)

(56) References Cited

U.S. PATENT DOCUMENTS

| | | | |
|---|---|---|---|
| 5,599,305 A * | 2/1997 | Hermann | A61B 17/12036 604/200 |
| 5,606,981 A | 3/1997 | Tartacower et al. | |
| 5,762,615 A * | 6/1998 | Weier | A61M 25/09 600/585 |
| 6,113,557 A | 9/2000 | Fagan et al. | |
| 7,044,921 B2 * | 5/2006 | Asmus | A61M 25/09 128/898 |
| 9,477,147 B2 * | 10/2016 | Chapman | F16C 1/10 |
| 9,918,705 B2 * | 3/2018 | Giles | A61B 17/00234 |
| 2003/0163064 A1 * | 8/2003 | Vrba | A61M 25/09 600/585 |
| 2006/0167384 A1 | 7/2006 | Kato | |
| 2007/0149951 A1 | 6/2007 | Wu et al. | |
| 2008/0064989 A1 * | 3/2008 | Chen | A61M 25/09 600/585 |
| 2009/0312747 A1 | 12/2009 | Delaney | |
| 2012/0265100 A1 * | 10/2012 | Maki | A61M 25/09 600/585 |

FOREIGN PATENT DOCUMENTS

| | | |
|---|---|---|
| JP | 2006-204386 A | 8/2006 |
| JP | 2007-190376 A | 8/2007 |
| JP | 2009-202030 A | 9/2009 |
| JP | 2012-205800 A | 10/2012 |

OTHER PUBLICATIONS

Written Opinion (PCT/ISA/237) dated Mar. 24, 2015, by the Japanese Patent Office as the International Searching Authority for International Application No. PCT/JP2015/052516.

English translation of the Notification of Reasons for Refusal dated Jul. 10, 2018, by the Japanese Patent Office in Japanese Patent Application No. 2016-508572 (4 pages).

Office Action (Notification of Reasons for Refusal) dated Dec. 4, 2018, by the Japanese Patent Office in corresponding Japanese Patent Application No. 2016-508572 and an English Translation of the Office Action. (9 pages).

* cited by examiner

GUIDEWIRE

CROSS-REFERENCES TO RELATED APPLICATIONS

This application is a continuation of International Application No. PCT/JP2015/052516 filed on Jan. 29, 2015, and claims priority to Japanese Patent Application No. 2014-057288 filed on Mar. 19, 2014, the entire content of both of which is incorporated herein by reference.

TECHNICAL FIELD

The present invention relates to a guidewire.

BACKGROUND ART

A guidewire is used for guiding a catheter to a treatment site in which it is difficult to perform a surgical operation, for example, percutaneous transluminal coronary angioplasty (PTCA). A guidewire may also be used to guide a catheter which is used for treatment that seeks to be less invasive to the human body, or a catheter used in diagnosis such as cardioangiography. The guidewire used in PTCA is inserted into the vicinity of a stenosed site of a blood vessel (i.e., a target site) together with a balloon catheter in a state in which a distal end of the guidewire is made to protrude from a distal end of the balloon catheter. The distal portion of the balloon catheter is then guided to the vicinity of the stenosed site of a blood vessel. The guidewire dilates the stenosed site of a blood vessel by passing through the stenosed site and guiding the distal portion of the balloon catheter to the stenosed site of the blood vessel.

The guidewire in the related art has a wire main body made primarily of super elastic alloy and a coil that covers a distal portion of the wire main body. For example, refer to the guidewire described in Japanese Patent Application No. 2009-202030. By providing such a configuration, it is possible to obtain sufficient flexibility in the distal portion and to reduce sliding resistance of the distal portion. It is thus possible to obtain a guidewire having excellent operability (such as blood vessel followability or blood vessel selectivity). However, several problems arise when performing the above-described treatment using this guidewire with a flexible distal portion.

A problem may arise in that it is difficult to obtain information about what degree the stenosed site of a blood vessel is stenosed (i.e., how much the stenosis is occluding the blood vessel). Specifically, an operator obtains information about the stenosed degree (i.e., degree of stenosis) by making the distal portion of the guidewire abut/contact the stenosed site of a blood vessel. If the distal end of the guidewire is flexible, however, it is difficult to obtain sufficient information (sensation or responses) to determine the stenosed degree of the stenosed site of a blood vessel even when the guidewire abuts/contacts the stenosed site of the blood vessel.

Another problem may arise in that it is difficult for the guidewire to pass through the stenosed site of a blood vessel if the distal portion of the guidewire is flexible. That is, if the distal portion of the guidewire is flexible, even if the guidewire is pushed in order to pass through the stenosed site of a blood vessel, the distal portion of the guidewire may bump into the stenosed site of a blood vessel and become curved and deformed. Therefore, it may be impossible to pass the stenosed site of a blood vessel as expected.

SUMMARY OF INVENTION

The guidewire and method of using a guidewire disclosed here can be used in accordance with medical procedures and is excellent in operability.

The guidewire disclosed here may include the following characteristics (1) to (10).

(1) A guidewire including: a wire main body which forms an elongated shape; a cylindrical body which forms a cylindrical shape and through which a distal portion of the wire main body is inserted; an inner coil which is disposed between the wire main body and the cylindrical body and is constituted of wire rods wound in a spiral shape along an outer circumferential portion of the wire main body, and in which the interval between the wire rods adjacent to each other in a longitudinal direction of the wire main body is variable; and an operation member which performs an operation of changing the interval.

(2) The guidewire according to the above-described (1), in which the rigidity of a distal portion of the guidewire is changed by changing the interval.

(3) The guidewire according to the above-described (1) or (2), in which the inner coil has radiopacity.

(4) The guidewire according to the above-described (3), in which the wire-rods function as scales and the interval between the scales is changed by changing the interval.

(5) The guidewire according to the above-described (3) or (4), in which, in the cylindrical body, radiopacity of an overlap portion overlapping the inner coil in a side view of the guidewire is lower than that of the inner coil.

(6) The guidewire according to the above-described (5), in which a portion of the cylindrical body other than the overlap portion has radiopacity which are the same as or larger than those of the inner coil.

(7) The guidewire according to any one of the above-described (1) to (6), in which the operation member is constituted of a tube through which the wire main body is inserted, and in which a distal portion of the operation member is interlocked to a proximal portion of the coil.

(8) The guidewire according to any one of the above-described (1) to (7), further including: a lock portion which maintains a state in which the interval is changed.

(9) The guidewire according to any one of the above-described (1) to (8), in which the cylindrical body is constituted of an outer coil which is formed by winding outer wire rods in a spiral shape.

(10) The guidewire according to the above-described (9), in which the outer wire rods adjacent to each other in a longitudinal direction of the wire main body are closely contact to each other regardless of the change in the interval.

Another aspect of the guidewire here involves a guidewire that includes a wire main body elongated in a longitudinal direction and a cylindrical body. The distal portion of the wire main body is within the cylindrical body such that the outer circumferential surface of the wire main body faces the inner circumferential surface of the cylindrical body and such that a space exists between the wire main body and the cylindrical body. The cylindrical body is attached to the wire main body so that they move together. The guidewire also includes an inner coil extending in the longitudinal direction. The inner coil is in the space between the wire main body and the cylindrical body in a radial direction of the guidewire. The inner coil includes a wound wire rod that is wound in a spiral shape along the outer circumferential surface of the wire main body. The wound wire rod includes windings that are adjacent to one another in the longitudinal direction and that are spaced apart from one another by an interval. The inner coil is fixed to the wire main body at a distal end of the inner coil so that they move together. The guidewire further has an operation member operatively connected to the inner coil. The operation member is configured to move in the longitudinal direction relative to the wire main body and the cylindrical body to change the interval between the adjacent wire rod windings of the inner coil and thereby vary the rigidity of the guidewire.

The method disclosed here includes inserting a guidewire into a blood vessel in a living body, moving the distal portion of the guidewire in a forward direction within the blood vessel to a stenosis site, increasing the rigidity of the distal portion while the guidewire is in the blood vessel, and moving the distal portion of the guidewire in the blood vessel in the forward direction after increasing the rigidity of the distal portion of the distal portion of the guidewire.

The catheter disclosed here makes it possible to appropriately change rigidity of the distal portion of the guidewire as needed in different medical procedures by changing the interval between the wire rods of the inner coil. Accordingly, the complicated operations of exchanging various guidewires having different rigidities (as in the technique in the related art) and using different guidewires is omitted. The guidewire disclosed here is thus excellent in operability.

In addition, when the wire rods of the inner coil function as scales, the interval between the scales may be changed in accordance with the medical procedure or the subject of the medical procedure by changing the interval between the wire rods. Accordingly, it is possible to set the inner coil on a lesion area without excess and deficiency (the inner coil can be appropriately sized for the patient's characteristics) when the distal portion of the guidewire is placed in the lesion area. Therefore, it is possible to accurately measure the length of the lesion area. Thus, the guidewire disclosed here provides excellent operability.

DETAILED DESCRIPTION

Embodiments for Carrying Out Invention

Set forth below is a detailed description of embodiments of a guidewire representing examples of the inventive guidewire disclosed here. Note that, for the convenience of description, there are cases where the dimensional ratios of the drawings are exaggerated and are different from the actual ratios.

First Embodiment

Figure 1:
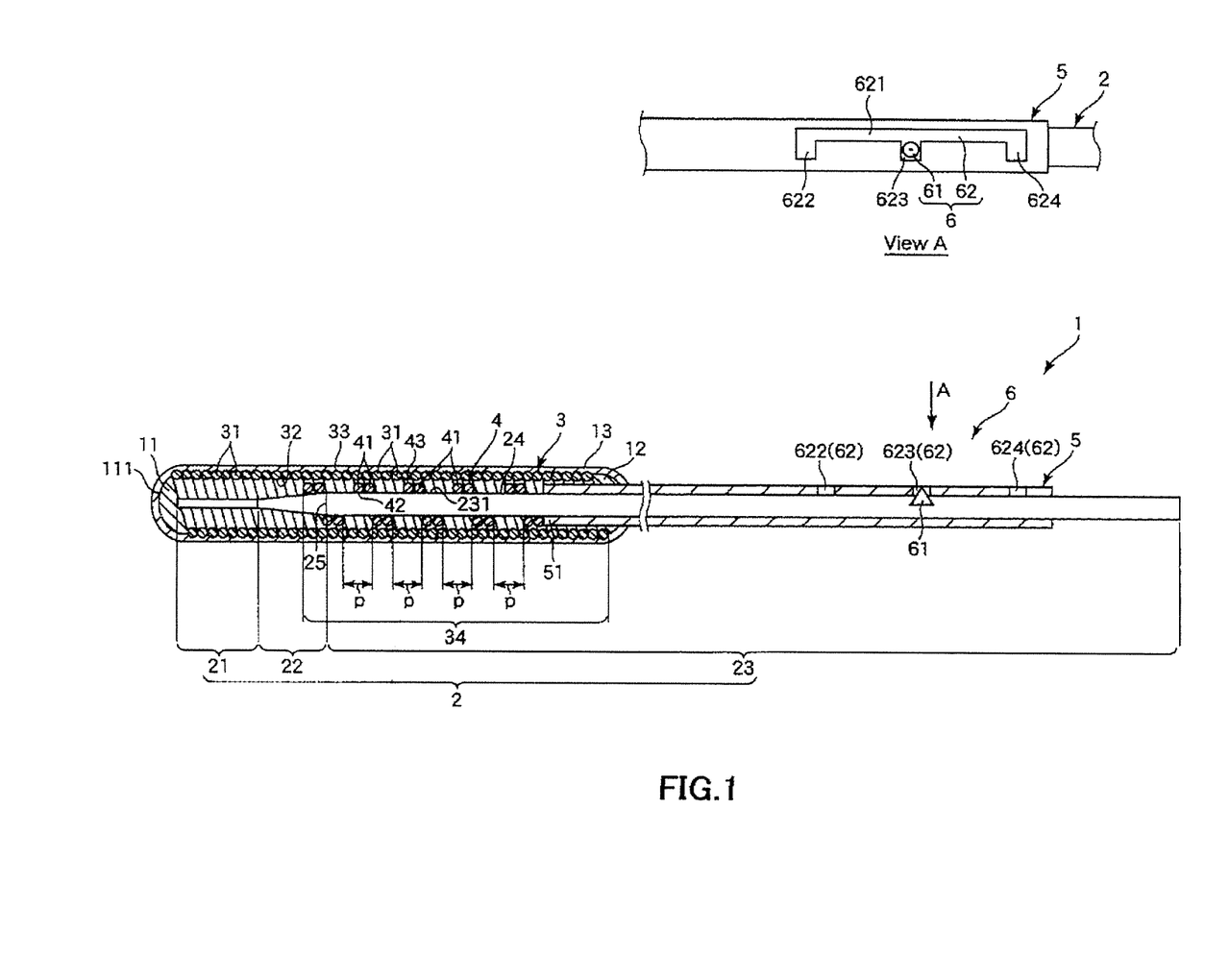
FIG. 1 is a partial longitudinal sectional view sequentially showing an operation process of one embodiment of a guidewire.
Figure 2:
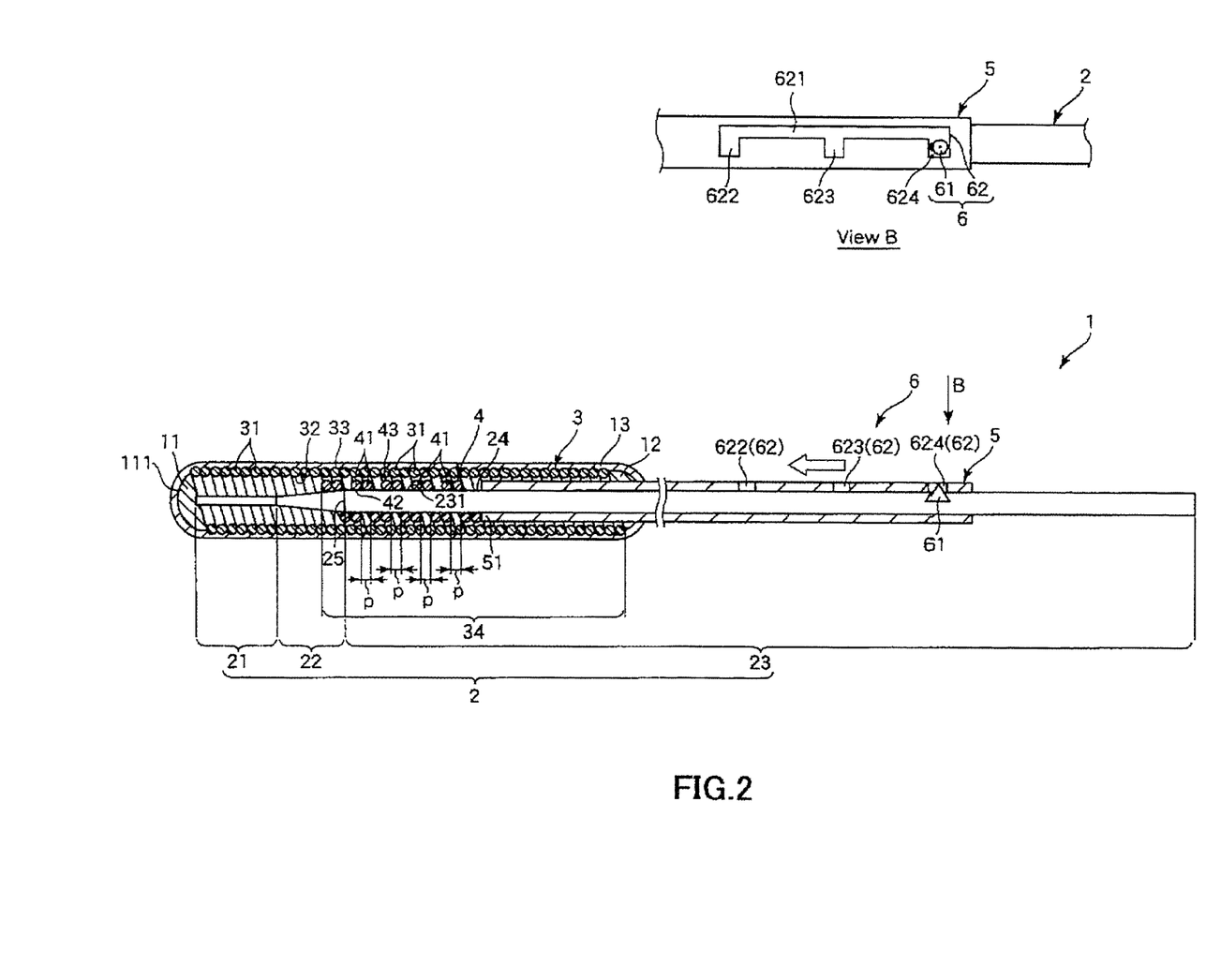
FIG. 2 is a partial longitudinal sectional view sequentially showing the operation process of the embodiment of the guidewire.

FIGS. 1 and 2 are respectively partial longitudinal sectional views showing operation processes of the guidewire (first embodiment) of the disclosed guidewire. In this description, a right side and a left side in FIGS. 1 and 2 (the same also applies to FIG. 3) are respectively referred to as a "proximal end" or "proximal side" and a "distal end" or a "distal side" for the convenience of description. In addition, the guidewire is schematically shown in FIGS. 1 and 2 (the same also applies to FIG. 3) by shortening the longitudinal direction of the guidewire and exaggerating the thickness direction of the guidewire for easier observation/clarity. The proportion of the longitudinal direction to the thickness direction is greatly different from the reality.

A guidewire 1 shown in FIGS. 1 and 2 includes a wire main body 2, an outer coil 3, an inner coil 4, and an operation member 5. The total length of this guidewire 1 is not particularly limited. When the guidewire 1 is used in, for example, a peripheral region by being inserted from a lower limb, the total length of this guidewire 1 is preferably 1500 mm to 3500 mm and more preferably 1800 mm to 3000 mm.

The wire main body 2 is constituted of an elongated body which forms an elongated shape and has flexibility (i.e., is flexible). This wire main body 2 has a small-diameter portion 21, a tapered portion 22, and a large-diameter portion 23 which are sequentially disposed from a distal end toward a proximal end (i.e., the small-diameter portion 21 is distal to the tapered portion 22 and the tapered portion 22 is distal to the large-diameter portion 23).

The small-diameter portion 21 is a constant outer diameter portion (first constant outer diameter portion). In other words, the outer diameter of the small-diameter portion 21 is constant along a longitudinal direction of the wire. The small-diameter portion 21 is a portion of the wire main body 2 where the size is minimized in the wire main body 2.

The tapered portion 22 is a portion of which the outer diameter decreases toward the distal side, and is continuously provided at a proximal end of the small-diameter portion 21 (i.e., the tapered portion 22 extends proximally starting from the proximal-most end of the small-diameter portion 21). Note that the taper angle (which also can be called a "decrease rate of an outer diameter") of the tapered portion 22 is constant along the longitudinal direction of the wire in the configuration shown in the drawing. However, the taper angle is not limited to a constant taper angle. There may be a taper angle which changes (i.e., is variable) along the longitudinal direction of the wire. In this case, for example, a configuration may have a plurality of portions of which the taper angle is comparatively large and a plurality of portions of which the taper angle is comparatively small and these portions may be alternately formed.

In addition, it is possible to gradually reduce the rigidity (flexural rigidity or torsional rigidity) of the wire main body 2 toward a distal direction using the tapered portion 22. As a result, the guidewire 1 can obtain favorable flexibility at the distal portion, improve followability (i.e., maneuverability) to a blood vessel and safety, and prevent bending or the like.

The large-diameter portion 23 is continuously provided at a proximal end of the tapered portion 22 (i.e., the large-diameter portion 23 continuously extends proximally from the proximal end of the tapered portion 22). The large-diameter portion 23 is a constant outer diameter portion (second constant outer diameter portion). In other words, the outer diameter of the large-diameter portion 23 is constant along a longitudinal direction of the wire. The large-diameter portion 23 is a portion of the wire main body where the size is maximized in the wire main body 2.

In addition, the wire main body 2 is a continuous linear body. The constituent material of the wire main body 2 is not particularly limited. Examples of materials that may be used for the wire main body include various metal materials. Among these, super elastic alloy is particularly preferable. All kinds of super elastic alloy which are greatly deformed (distorted) by a stress or almost return to an original shape due to removal of a stress are included in addition to super elastic alloy which has any shape of stress-strain curves due to pulling and super elastic alloy which can or cannot noticeably measure a transformation point such as Ms, Mf, As, and Af. Here, "Ms" is a temperature at which martensitic transformation starts, "Mf" is a temperature at which martensitic transformation finishes, "As" is a temperature at which reverse transformation starts, and "Af" is a temperature at which reverse transformation finishes. Examples of preferred compositions of super elastic alloy include Ni—Ti based alloy such as Ni—Ti alloy with 49 to 52 atom % Ni, Cu—Zn alloy with 38.5 to 41.5 wt % Zn, Cu—Zn—X alloy with 1 to 10 wt % X (X is at least one of Be, Si, Sn, Al, or Ga), and Ni—Al alloy with 36 to 38 atom % Al. Among these, Ni—Ti based alloys are particularly preferable.

Super elastic alloys are comparatively flexible and have resilience. Super elastic alloys are resistant to bending. Therefore, sufficient flexibility and resilience with respect to bending are obtained in the guidewire 1. This allows for excellent operability due to improved followability with respect to blood vessels which are curved and bent (i.e., improved maneuverability within curved/bent blood vessels). Even if the guidewire 1 repeats deformation of curving and bending, the guidewire 1 has resilience and so undesired bending may be avoided. Therefore, it is possible to prevent deterioration in operability due to the tendency to bend occurring when using the guidewire 1.

The outer coil 3 is provided at the distal portion of the wire main body 2 as a cylindrical body which forms a cylindrical shape (i.e., the wire main body 2 is cylindrically shaped). The inner diameter and the outer diameter of the outer coil 3 are respectively constant along the longitudinal direction of the wire.

The wire main body 2 is inserted into this outer coil 3 from the small-diameter portion 21 to the middle of the large-diameter portion 23 (i.e., the wire main body 2 overlaps the outer coil 3 in the axial direction from the distal end of the small-diameter portion 21 to the middle of the large-diameter portion 23). In addition, an inner circumferential portion 32 of the outer coil 3 and an outer circumferential portion of the wire main body 2 are separated from each other, and a gap is formed between the inner circumferential portion 32 of the outer coil 3 and the outer circumferential portion of the wire main body 2 (i.e., the outer coil 3 and the wire main body 2 are spaced apart in the radial direction).

The distal portion of the outer coil 3 is fixed to the small-diameter portion 21 of the wire main body 2 through, for example, a fixation material 11 such as solder (brazing material). A distal end 111 of the fixation material 11 is preferably rounded.

In addition, the fixation member 12 is fixed to the proximal portion of the outer coil 3. A fixation member 12 forms a ring shape and is formed of, for example, solder (brazing material), an adhesive, or the like. The outer coil 3 is a coil of wire rods (outer wire rods) 31 that are wound in a spiral shape along a circumferential direction of the outer circumferential portion 24 of the wire main body 2. These wire rods 31 is densely wound. Specifically, the wire rods 31 which are adjacent in the longitudinal direction of the wire are in close contact with each other (i.e., each of the wire rods 31 are in contact with the adjacent wire rod(s) 31). The densely wound state of the wire rods 31 is maintained due to characteristics of the material of the wire rods 31, but is also maintained by a hydrophilic layer 13 which is described below.

The wire rods 31 are preferably made of metal materials. Examples of the metal materials include stainless steel, super elastic alloy, cobalt-based alloy, noble metal such as gold, platinum, and tungsten, or alloy containing these kinds of noble metal. In a case where the wire rods are made of radiopaque materials such as noble metal, the guidewire 1 can obtain X-ray radiopacity so that it is possible to insert the guidewire 1 into a living body while checking the position of the distal portion under X-ray fluoroscopy.

The wire diameters (outer diameters) of the wire rods 31 depicted are constant, but the wire rods 31 do not necessarily have to have constant diameters. In addition, the sizes of the wire rods 31 (outer diameters of the wire rods 31) are preferably the same as or smaller than those of the small-diameter portion 21 of the wire main body 2.

The outer coil 3 may contribute to improved resilience with respect to bending, along with the wire main body 2 made of super elastic alloy.

In addition, the hydrophilic layer 13 coated with a hydrophilic material is provided on an outer circumferential portion 33 of the outer coil 3. This hydrophilic layer 13 also covers the fixation material 11 and/or the fixation member 12. The hydrophilic layer 13 generates lubricity due to wet hydrophilic materials/properties. Friction generated by the guidewire 1 is thus reduced. Therefore, sliding properties (e.g., within a living body) are improved. Accordingly, the operability of the guidewire 1 is improved. Examples of the hydrophilic materials include cellulose-based polymeric substances, polyethylene oxide-based polymeric substances, maleic anhydride polymeric substances (for example, maleic anhydride copolymer such as methyl vinyl ether-maleic anhydride copolymers), acrylamide-based polymeric substances (for example, polyacrylamide and a polyglycidyl methacrylate-dimethylacrylamide (PGMA-DMAA) block copolymer), water-soluble nylon, polyvinyl alcohol, and polyvinylpyrrolidone.

The inner coil 4 is disposed between the wire main body 2 and the outer coil 3. The inner coil 4 is freely stretchable (i.e., compressible/extendable) along the longitudinal direction of the wire (refer to FIGS. 1 and 2). The natural length of the inner coil when no external force is applied is shorter than the total length of the outer coil 3.

The wire main body 2 is inserted into this inner coil 4 from the tapered portion 22 to the middle of the large-diameter portion 23 (i.e., at least a portion of the tapered portion 22 and the large diameter portion 23 of the wire main body 2 overlap with the inner coil 4 in the axial direction). The distal portion of the inner coil 4 is fixed to the vicinity of a boundary portion 25 between the tapered portion 22 and the large-diameter portion 23 (i.e., the distal portion of the inner coil 4 is attached/connected to the outer surface of the wire main body 2 in the vicinity of the boundary portion 25). The proximal portion of the inner coil 4 is fixed (interlocked) to a distal portion 51 of the operation member 5. The fixation method is not particularly limited. Examples of fixation methods include a method performed through fitting, a method performed through engagement, a method performed through adhesion (adhesion using an adhesive or a solvent), a method performed through fusion (heat-welding, high-frequency fusion, ultrasonic fusion, or the like), a method using a fixation material such as solder (brazing material), and a method in which these methods are combined.

Figure 3:
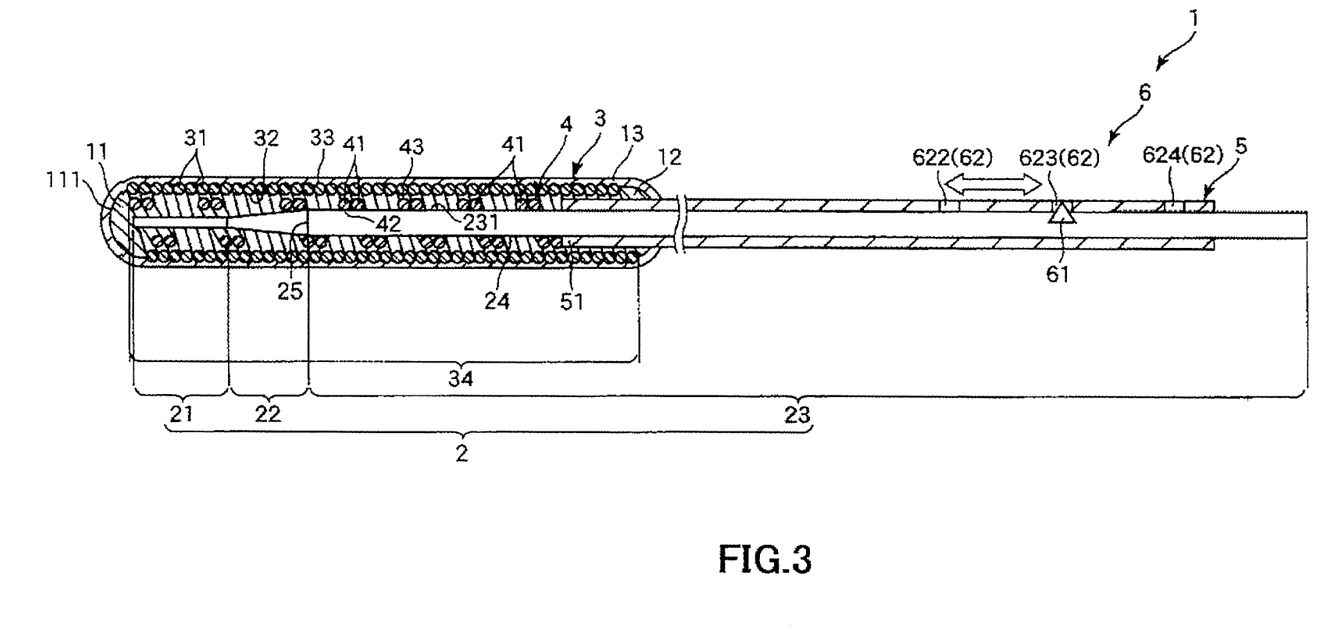
FIG. 3 is a partial longitudinal sectional view showing another embodiment.

As shown in FIGS. 1 and 2, the inner coil 4 is a coil in which wire rods (inner wire rods) 41 are wound in a spiral shape along the outer circumferential portion 24 of the wire main body 2 (i.e., along and in contact with the outer surface of the wire main body 2). The winding direction (i.e., pitch angle) of the wire rods 41 may be the same as or different from the winding direction of the wire rods 31. If the winding direction of the wire rods 41 is the same as that of the wire rods 31 (as shown in FIGS. 1-3), the guidewire has a structure which is more easily deformed by bending stress compared to when the winding direction of the wire rods 41 is different from that of the wire rods 31. In contrast, if the winding direction of the wire rods 41 is different from the winding direction of the wire rods 31 (i.e., the pitch angle of the wire rods 41 is oriented in the opposite direction as the pitch angle of the wire rods 31), there is an advantage in that the guidewire has a structure which is more resistant to deformation by bending stress.

These wire rods 41 have a densely wound portion and a roughly wound portion. That is, there is a portion of the inner coil 4 in which the wire rods 41 adjacent to each other in the longitudinal direction of the wire are closely contact to each other (i.e., densely wound), and a portion in which the wire rods 41 are separated from each other. In the separated portion, an interval p between the adjacent wire rods is variable (i.e., adjustable). Note that an operation of changing the interval p is performed by the operation member 5 (i.e., moving the operation member 5 changes the interval p).

As the interval p between adjacent wire rods 41 is decreased, the rigidity of the entirety of the inner coil 4 increases (i.e., the inner coil 4 becomes more rigid). As a result, the rigidity of the distal portion (which is a portion covered by the outer coil 3) of the guidewire 1 also increases (e.g., see FIG. 2 illustrating increased rigidity compared to FIG. 1). In contrast, as the interval p between adjacent wire rods 41 increases, the rigidity of the entirety of the inner coil 4 decreases (i.e., the inner coil 4 becomes less rigid). As a result, the rigidity of the distal portion of the guidewire 1 is reduced and exhibits flexibility (e.g., see FIG. 1 illustrating decreased rigidity compared to FIG. 2). In this manner, the rigidity of the distal portion of the guidewire 1 is incrementally adjusted/changed by changing the interval p between the adjacent wire rods 41.

There are various lesion areas within blood vessels, for example, calcified sites or stenosed sites which are remarkably stenosed. It is preferable to place the guidewire in a high rigidity state as shown in FIG. 2 in order to pass through these types of lesion areas. Placing the guidewire in a high rigidity state (e.g., as shown in FIG. 2) makes it is possible for the distal portion of the guidewire 1 to easily and reliably pass the lesion areas.

In addition, it is preferable to make the guidewire 1 enter a relatively flexible state as shown in FIG. 1 during a period until the distal portion of the guidewire 1 reaches a lesion area after being inserted into a blood vessel. The relatively flexible state of the guidewire 1 allows the distal portion of the guidewire 1 to follow the curved shape of a blood vessel. Therefore, it is possible to make the distal portion of the guidewire 1 to be maneuvered promptly and reliably close to the lesion area.

An operation can thus be performed using one guidewire 1 including the guidewire passing the lesion area after being inserted into the blood vessel. Accordingly, the operational complexity of exchanging various guidewires having different rigidities (as in the technique in the related art) and using various guidewires is omitted in accordance with the medical procedure. Accordingly, the guidewire 1 is excellent in operability and it is possible to perform a prompt technique.

FIGS. 1 and 2 illustrate two examples of the interval p, but it is possible to appropriately change the interval p in accordance with the state of the lesion area or the curved state of the blood vessel.

In addition, the wire rods 31 adjacent in the longitudinal direction of the wire of the outer coil 3 are closely contacted to each other regardless of the change in the interval p (i.e., the adjacent wire rods 31 remain in contact with one another throughout the operation, even as the interval p changes). If the outer coil 3 is omitted, there may be a concern that the inner coil 4 (of which the interval p changes) may contact to harm/damage a blood vessel wall. In the guidewire 1, however, the densely wound outer coil 3 is disposed outside the inner coil 4. Therefore, it is possible to reliably prevent the blood vessel wall from being harmed/damaged.

In addition, if the outer coil 3 is omitted, it is difficult to provide the hydrophilic layer 13 in the outer circumferential portion 43 of the inner coil 4 because the interval p changes in the inner coil 4 (i.e., the interval p between adjacent wire rods 41 of the inner coil 4 is adjustable). In the guidewire 1, however, it is possible to provide the hydrophilic layer 13 in the outer coil 3. Therefore, the guidewire has a configuration for improving sliding properties.

As shown in FIGS. 1 and 2, when the inner coil 4 stretches and contracts; the inner circumferential portion 42 slides on (i.e., sliding while in contact with) the outer circumferential portion 231 of the large-diameter portion 23. Accordingly, the inner coil 4 is guided to the large-diameter portion 23, and the stretching/contracting operation is stably performed.

The outer circumferential portion 43 of the inner coil 4 is separated from (i.e., spaced apart from) the inner circumferential portion 32 of the outer coil 3 regardless of the change in the interval p. Accordingly, it is possible to prevent the biting between the inner coil 4 and the outer coil 3. For example, if the inner coil 4 and the outer coil 3 are bitten (i.e., contact one another), there is a concern that a certain wire rod 31 of the outer coil 3 may be stranded on a wire rod 31 adjacent thereto (i.e., the certain wire rod 31 may be forced into displacement/misalignment relative to the other wire rods 31 when the inner coil 4 is not spaced apart from the inner circumferential portion 32 of the outer coil 3 because the inner coil 4 is moved to change the interval p by compressing/expanding in the longitudinal direction). The configuration of the guidewire 1, however, makes it possible to prevent the wire rods from being stranded in this manner.

The wire rods 41 which form the inner coil 4 are made of radiopaque materials such as noble metal such as gold, platinum, and tungsten. Accordingly, it is preferable in that the inner coil 4 can obtain X-ray radiopacity and it is possible to insert the guidewire 1 into a living body while checking the position of the distal portion of the guidewire 1 under X-ray fluoroscopy.

The wire rods 41 may also function as a length-measuring scale for measuring the total length of a lesion area under X-ray fluoroscopy. If the size of an interval p is known, it is possible to measure the total length of the lesion area by counting the number of intervals p which overlap the lesion area when the distal portion of the guidewire 1 is moved to the lesion area.

When measuring the length of the lesion area, the interval p may be changed in accordance with the age of a patient (subject). It is may be necessary to set the width for length measurement for an adult (grown-up) compared to that of a child (minor). For this reason, it is preferable to set the state of the interval p for an adult to be large as shown in FIG. 1 and to set the state of the interval p for a child to be small as shown in FIG. 2. Accordingly, the interval of a scale is changed depending on medical cases (e.g., the procedure and/or the subject of the procedure). It is possible to set the inner coil 4 on a lesion area without excess and deficiency (e.g., the wire rods 41 of the inner coil 4 can be appropriately set/spaced based on the patient's characteristics) when the distal portion of the guidewire 1 is placed in the lesion area, and therefore, it is possible to accurately measure the length of the lesion area.

In the state shown in FIG. 1, the interval p is preferably 25 to 45 mm and more preferably 30 to 40 mm. In addition, in the state shown in FIG. 2, the interval p is preferably 10 to 20 mm.

The wire diameters of the wire rods 41 are preferably the same as or larger (i.e., greater in diameter) than those of the wire rods 31. Accordingly, the wire rods 41 which function as scales become easily visible under X-ray fluoroscopy.

An overlap portion 34 overlapping the inner coil 4 in a most stretching state (i.e., when the inner coil 34 is fully expanded/stretched in the longitudinal direction) in the outer coil 3 in a side view of the guidewire 1 has lower radiopacity than those of the inner coil 4. Accordingly, it is possible to prevent inhibition of viewing the radiopacity of the inner coil 4 in the overlap portion 34 under X-ray fluoroscopy. Therefore, it is possible to reliably use the function of measuring the length of the inner coil 4.

The remaining portion other than the overlap portion 34 of the outer coil 3 has radiopacity which is the same as or larger than that of the inner coil 4. Accordingly, radiopacity can be secured as the entirety of the distal portion of the guidewire 1.

Note that the method for reducing radiopacity of the overlap portion 34 and causing radiopacity of the remaining portion other than the overlap portion to be greater than or equal to those of the inner coil 4 is not particularly limited. Examples of increasing/decreasing the radiopacity include a method for changing the constituent material of the overlap portion and the inner coil.

The operation member 5 is a member which performs an operation of changing the interval p. The operation member 5 is constituted of a tube through which the wire main body 2 is inserted. The total length of the operation member 5 is shorter than that of the wire main body 2. The distal portion 51 of the operation member 5 is interlocked and fixed to the proximal portion of the inner coil 4.

FIG. 2 illustrates a state after the state shown in FIG. 1. An operator moves the guidewire 1 into the state shown in FIG. 2 by pressing the operation member 5 distally relative to the wire main body 2 in an arrow direction in FIG. 2. The pressing force is transmitted the inner coil 4. Accordingly, the inner coil 4 reliably contracts (is compressed) and the interval p is reduced. In addition, an operator may increase the interval p by pulling the operation member 5 with respect to the wire main body 2 in a direction opposite to the arrow direction (i.e., causing the operation member 5 to move proximally relative to the wire main body 2). The pulling force is thus transmitted to the inner coil 4 to stretch/elongate the inner coil 4 reliably stretches (i.e., the interval p is increased).

The material of the operation member 5 is not particularly limited. For example, it is possible to use materials which have been exemplified as the constituent materials of the wire main body 2.

A lock mechanism portion (lock portion) 6 which maintains a state in which the interval p is changed (i.e., the interval p is held constant/fixed by the lock mechanism portion 6) is provided in the guidewire 1. Accordingly, even if an operator releases the operation member 5 after the change of the interval p, the changed interval p is maintained. Therefore, the operability is improved.

As shown in FIGS. 1 and 2, the lock mechanism portion 6 is constituted of a protruding portion 61 and a slit 62. The protruding portion 61 protrudes from the middle of the large-diameter portion 23 of the wire main body 2. The slit 62 is provided by penetrating the operation member 5.

The protruding portion 61 is, for example, conically shape. This protruding portion 61 may be formed integrally with the wire main body 2, or may be formed separately from the wire main body 2 so as to join the separate body to the wire main body 2.

The slit 62 is constituted of a first slit 621 which is formed along the longitudinal direction of the operation member 5, and second slits 622, 623, and 624 which are formed so as to communicate with the first slit 621 along the circumferential direction of the operation member 5 (i.e., the second slits 622, 623, 624 extend in the circumferential direction from the first slit 621). The second slit 622 is disposed at a distal portion of the first slit 621. Another second slit 623 is disposed in a central portion of the first slit 621 in the longitudinal direction. Another second slit 624 is disposed at a proximal portion of the first slit 621.

In the lock mechanism portion 6, the protruding portion 61 can be engaged with (i.e., seated within) any of the second slits 622 to 624. For example, the interval p in the state shown in FIG. 1 is maintained by the protruding portion 61 being engaged with (i.e., seated within) the second slit 623, and the interval p in the state shown in FIG. 2 is maintained by the protruding portion 61 being engaged with (i.e., seated within) the second slit 624.

The protruding portion 61 can pass through the first slit 621 when, for example, being transferred from the second slit 623 to another second slit 624.

In another example of the configuration of the lock mechanism portion 6, the lock mechanism portion may be constituted of a female screw and a male screw. The female screw is provided in the outer circumferential portion of the wire main body 2, and the male screw is provided in the inner circumferential portion of the operation member 5 and is screwed into the female screw. By doing this, it is possible to perform fine adjustment through advancing or retracting through rotation of the male screw.

Second Embodiment

FIG. 3 is a partial longitudinal sectional view showing a second embodiment of the guidewire disclosed here.

The second embodiment of the guidewire will be described while referring to FIG. 3. The description below explains the difference between the second embodiment and the above-described embodiment, and the same matters (i.e., common features) will not be repeated.

The present embodiment is the same as the first embodiment except that the installation state of the inner coil in the first embodiment is different from that of the present embodiment.

In the embodiment depicted in FIG. 3, a distal portion of an inner coil 4 is fixed to a small-diameter portion 21 of a wire main body 2 through a fixation material 11 along with a distal portion of an outer coil 3. In this manner, the fixation material 11 fixes both of the inner coil 4 and the outer coil 3 in this embodiment. Accordingly, it is possible to simplify the configuration of a guidewire 1 compared to a case where portions which fix the inner coil 4 and the outer coil 3 are respectively separately provided.

The embodiment of the guidewire disclosed here which is shown in the drawing has been described above. However, the guidewire is not limited to the disclosed embodiments. For example, wire rods 41 have the same diameters from a distal side to a proximal side. However, a guidewire may have a configuration in which the diameters of the wire rods are gradually increased or decreased from the distal side over the proximal side (i.e., tapered). In addition, intervals p of the inner coil 4 are equal intervals from the distal side to the proximal side. However, the guidewire is not limited to this configuration and may have a configuration in which the intervals gradually become wide or narrow from the distal side over the proximal side. The above-described configuration can provide variation in the change of rigidity of the distal portion.

In addition, each portion constituting the guidewire can be substituted with an arbitrary configuration which can exhibit the same function. Additional components may be added to the guidewire.

Two or more arbitrary structures (characteristics) in each of the embodiments may also be combined with each other.

In addition, the wire main body 2 may be made of stainless steel of which the rigidity is higher than that of super elastic alloy. The wire main body 2 may also be obtained by joining a first wire, which is disposed on the proximal side and is made of stainless steel, and a second wire, which is disposed on the distal side and is made of super elastic alloy, to each other.

In addition, the cylindrical body provided at the distal portion of the wire main body is an outer coil which is formed by winding wire rods in a spiral shape in each embodiment. However, the guidewire is not limited to this configuration and may a resin pipe made of, for example, resin material such as polyurethane.

The guidewire includes: a wire main body which forms an elongated shape; a cylindrical body which forms a cylindrical shape and through which a distal portion of the wire main body is inserted; an inner coil which is disposed between the wire main body and the cylindrical body and is constituted of wire rods wound in a spiral shape along an outer circumferential portion of the wire main body, and in which the interval between the wire rods adjacent to each other in a longitudinal direction of the wire main body is variable; and an operation member which performs an operation of changing the interval. For this reason, the guidewire disclosed here can be used in accordance with medical procedures and is excellent in operability.

Accordingly, the guidewire of the present invention has industrial applicability.

The detailed description above describes a medical device and treatment method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A guidewire comprising:
   a wire main body possessing an elongated shape, an outer circumferential portion, and a distal portion, the wire main body extending in a longitudinal direction;
   an outer wound coil possessing a cylindrical shape, the distal portion of the wire main body being positioned in the outer wound coil, the outer wound coil comprising windings wound in a spiral shape;
   an inner coil disposed between the wire main body and the outer wound coil, the inner coil comprising a wire rod wound in a spiral shape along and in contact with the outer circumferential portion of the wire main body, and an interval between the wire rods adjacent to each other in a longitudinal direction of the wire main body being adjustable; and
   an operation member configured to change the interval between the wire rods of the inner coil.

2. The guidewire according to claim 1, wherein a rigidity of the distal portion of the guidewire is changed by changing the interval.

3. The guidewire according to claim 1, wherein the inner coil has radiopacity.

4. The guidewire according to claim 3, wherein the wire rods function as scales and a spacing between the scales is changed by changing the interval.

5. The guidewire according to claim 3, wherein
   the outer wound coil possesses an overlap portion that overlaps with the inner coil in the longitudinal direction, and
   radiopacity of the overlap portion overlapping the inner coil is lower than the radiopacity of the inner coil.

6. The guidewire according to claim 5, wherein an other portion of the outer wound coil other than the overlap portion has radiopacity which is the same as or greater than the radiopacity of the inner coil.

7. The guidewire according to claim 1, wherein
   the operation member comprises a distal portion and a tube in which the wire main body is positioned, and
   the distal portion of the operation member is interlocked to a proximal portion of the coil.

8. The guidewire according to claim 1, further comprising:
   a lock which is configured to maintain the interval between the adjacent wire rods of the inner coil.

9. The guidewire according to claim 1, wherein the outer wound coil is formed by winding outer wire rods in a spiral shape.

10. The guidewire according to claim 9, wherein the outer wire rods adjacent to each other in the longitudinal direction of the wire main body remain in contact to each other regardless of the change in the interval.

11. The guidewire according to claim 1, wherein the inner coil possesses a length when no external force is applied to the inner coil, the outer wound coil possessing a length, and the length of the inner coil when no external force is applied being shorter than the length of the outer wound coil.

12. The guidewire according to claim 1, wherein
   the wire main body comprises a first linear portion, a tapered portion distal to the first linear portion, and a second linear portion distal to the tapered portion, the second linear portion including the distal end of the wire main body, and
   the inner coil being fixed at the second linear portion of the wire main body distal to the tapered portion of the wire main body.

13. The guidewire according to claim 1, wherein the outer wound coil possesses a length in the longitudinal direction, the length of the outer wound coil remaining constant when the interval between the wire rods of the inner coil is changed.

14. A guidewire comprising:
   a wire main body elongated in a longitudinal direction, the wire main body possessing an outer circumferential surface and a distal portion;

a cylindrical body comprising an inner circumferential surface, the distal portion of the wire main body being located within the cylindrical body such that the outer circumferential surface of the wire main body faces the inner circumferential surface of the cylindrical body and such that a space exists between the outer circumferential surface of the wire main body and the inner circumferential surface of the cylindrical body, the cylindrical body being attached to the wire main body so that the cylindrical body and the wire main body move together, the cylindrical body possessing a length in the longitudinal direction;

an inner coil extending in the longitudinal direction, the inner coil being in the space between the wire main body and the cylindrical body in a radial direction of the guidewire, the inner coil comprising a wound wire rod that is wound in a spiral shape along the outer circumferential surface of the wire main body, the wound wire rod including windings that are adjacent to one another in the longitudinal direction and that are spaced apart from one another by an interval, the inner coil being fixed to the wire main body at a distal end of the inner coil so that the distal end of the inner coil moves together with the wire main body; and an operation member operatively connected to the inner coil, the operation member being configured to move in the longitudinal direction relative to the wire main body and the cylindrical body to change the interval between the adjacent wire rod windings of the inner coil and thereby vary rigidity of the guidewire, the length of the cylindrical body remaining constant throughout the changing of the interval between the adjacent wire rod windings of the inner coil.

15. The guidewire according to claim 14, wherein the operation member is configured to be moved in a distal direction relative to the wire main body and relative to the cylindrical main body to decrease the interval between the adjacent wire rod windings of the inner coil to increase rigidity of a distal portion of the guidewire.

16. The guidewire according to claim 15, wherein the inner coil comprises a plurality of wire rods round in the spiral shape.

17. The guidewire according to claim 15, further comprising
a locking mechanism protruding from the wire main body, the locking mechanism operatively engaging the operation member to fix the interval.

* * * * *